(12) United States Patent
Fisher et al.

(10) Patent No.: US 7,754,232 B2
(45) Date of Patent: Jul. 13, 2010

(54) ULTRASONIC MODIFICATION OF SOFT TISSUE MATRICES

(75) Inventors: John Fisher, Leeds (GB); Eileen Ingham, Leeds (GB)

(73) Assignee: The University of Leeds, Leeds (GB)

( * ) Notice: Subject to any disclaimer, the term of this patent is extended or adjusted under 35 U.S.C. 154(b) by 0 days.

(21) Appl. No.: 10/557,779

(22) PCT Filed: May 14, 2004

(86) PCT No.: PCT/GB2004/002055

§ 371 (c)(1),
(2), (4) Date: Nov. 18, 2005

(87) PCT Pub. No.: WO2004/103461

PCT Pub. Date: Dec. 2, 2004

(65) Prior Publication Data

US 2007/0041949 A1    Feb. 22, 2007

(30) Foreign Application Priority Data

May 22, 2003   (GB) .................................. 0311800.7

(51) Int. Cl.
*A61F 2/00* (2006.01)
(52) U.S. Cl. ....................................... 424/423; 600/437
(58) Field of Classification Search ................... None
See application file for complete search history.

(56) References Cited

U.S. PATENT DOCUMENTS

| 4,420,339 | A | * | 12/1983 | Kato ........................ 106/160.1 |
| 5,003,965 | A |   | 4/1991  | Talish et al. |
| 5,524,624 | A |   | 6/1996  | Tepper et al. |
| 5,899,937 | A | * | 5/1999  | Goldstein et al. ........... 623/2.11 |
| 2002/0119437 | A1 | * | 8/2002  | Grooms et al. ................. 435/2 |
| 2002/0183857 | A1 | * | 12/2002 | Yang ....................... 623/23.72 |
| 2003/0153849 | A1 |   | 8/2003  | Huckle et al. |

FOREIGN PATENT DOCUMENTS

| EP | 0 773 033 A1 | | 5/1997 |
| EP | 0773033 A1 | * | 5/1997 |
| WO | WO 96/40889 A1 | | 12/1996 |

OTHER PUBLICATIONS

Ramirez et al., Medicine & Science in Sports & Exercise, Mar. 1997, vol. 29, No. 3, p. 326-332.*
Abrams et al., Cells Tissues Organs, 2002, vol. 170, No. 4, p. 251-257.*
Chen et al., Urology, 1999, vol. 54, p. 407-410.*
Mitragotri et al., Pharmaceutical Research 1996, vol. 13, No. 3, p. 411-420.*
Hollister et al., Biomaterials 2002, vol. 23, p. 4095-4103.*
Yock et al., Circulation, 1997, vol. 95, p. 1360-1362.*
International Search Report, PCT/GB2004/002055, Sep. 1, 2004.
International Preliminary Report on Patentability, PCT/GB2004/002055, May 12, 2005.
Search Report Under Section 17, GB 0111393.5, Jul. 6, 2001.

* cited by examiner

*Primary Examiner*—L Blaine Lankford
*Assistant Examiner*—Kade Ariani
(74) *Attorney, Agent, or Firm*—Myers Bigel Sibley & Sajovec

(57) ABSTRACT

The present invention provides a method of, and apparatus for, utilizing ultrasonic energy so as to mechanically disrupt the collagenous architecture of biological matrices in a controlled manner so that the tissue can be rapidly recellularized in continuous form. The present invention also provides for the production of tissue matrices with improved recellularization properties, cell stratification or patterning.

26 Claims, 13 Drawing Sheets

MC =Mononuclear cell

MC =Mononuclear cell    DM =Disrupted matrix

MC = Mononuclear cell

MC =Mononuclear cell   DM =Disrupted matrix

ULTRASONIC MODIFICATION OF SOFT TISSUE MATRICES

RELATED APPLICATION

This application is a national phase application of PCT International Application PCT/GB2004/002055, filed May 14, 2004, and published in English on Dec. 2, 2004 as International Publication No. WO 2004/103461, which claims priority from British Application No. 0311800.7, filed May 22, 2003. These disclosures are hereby incorporated by reference herein in their entireties.

The present invention relates to a method of, and apparatus for, improving recellularisation of matrices or tissue engineered biomaterials, the matrices or tissue engineered biomaterials being for use particularly in implantation and wound healing.

BACKGROUND TO THE INVENTION

Tissue engineering involves the delivery of scaffold materials and/or living cells to repair and/or replace damaged, degenerative or dysfunctional tissues. Tissue engineered implants may be used for the clinical repair or replacement of damaged or degenerative tissues of a variety of tissues/organs.

Typically, tissue engineered implants comprise a scaffold material (either synthetic or biological in origin) which can be delivered as an acellular matrix that promotes or guides tissue regeneration or, as a 'living' composite, which has been seeded in vitro with viable cells prior to implantation. Ideally, the cells used in these 'living' implants have been isolated from the graft recipient's own tissue (autogeneic), however 'banked' cells from different donors (allogeneic) may also be used.

One approach to tissue engineering has been to construct tissue implants in vitro, starting from their component matrix and cellular elements, with or without the inclusion of a synthetic polymer scaffold, which may be required in order to provide mechanical strength during the initial period of matrix synthesis, reorganisation and maturation. The preformed architecture of natural tissue matrices offers a number of advantages over the use of synthetic materials and laboratory generated biological matrices. Primarily, implants engineered using natural matrices can more closely reproduce the biomechanical and functional properties of the replaced tissue without the need for mechanical 'pre-conditioning'. Natural matrices may be derived from either human (allogeneic) or non-human species (xenogeneic). Regardless of their source, they are frequently decellularised in order to reduce their immunogenicity. It is known in the prior art, as described in EP 0773033, to use an ultrasonic wash/bath at a low energy intensity to clean away/remove cellular layers from connective tissue membranes. Additionally, decellularisation can be achieved by biochemical modification using detergents, or enzymes. Additionally, cross-linking the component polymers is used to enhance their stability, and hence their longevity, in vivo. A problem associated with biochemically modified matrices is their resistance to rapid recellularisation. Biochemical modification such as cross-linking can render the tissue environment more hostile to infiltrating cells and hence delay recellularisation, a process that is considered essential for the restoration of biological function.

In an attempt to improve recellularisation, it is known from the prior art to coat the surface of the matrix with beneficial molecules, such as growth factors or adhesion molecules that promote cell attachment. However, even after coating the matrix surface there is a problem with encouraging the colonising cells to penetrate into the depths of the tissue so that they begin to remodel the existing structure and synthesise new extracellular matrix. Previous approaches to this problem (which affects cellular infiltration both in vitro and in vivo) have included mechanical or laser 'punching' of holes in the structure in a fine array. However, neither of these techniques are able to produce a continuous effect and they only allow cellular access to the region surrounding the holes and not the whole of the matrix. It is also known from the prior art to use jet injection technology to propel cells at a three dimensional matrix such that the cells become embedded within the interior of the matrix. This method is described in WO96/40889. However, the problem with this method is that the cells can become mechanically damaged due to the jet propulsion and eventually necrose.

A further attempt to improve recellularisation lies in the use of ice crystals which are formed during repeated freeze thawing or freeze-drying, the ice crystals may be used to disrupt the collagenous network. A disadvantage of this method is that the resultant physical changes are not only difficult to control and but can produce significant deterioration in the mechanical properties of treated tissues.

The present invention provides a novel technique which mitigates some of the prior art problems.

STATEMENT OF THE INVENTION

Various aspects of the present invention will now be described in more detail with respect to other embodiments described herein. It should be appreciated that the invention can be embodied in different forms and should not be construed as limited to the embodiments set forth herein. Rather, these embodiments are provided so that this disclosure will be thorough and complete, and will fully convey the scope of the invention to those skilled in the art.

The terminology used in the description of the invention herein is for the purpose of describing particular embodiments only and is not intended to be limiting of the invention. As used in the description of the invention and the appended claims, the singular forms "a," "an" and "the" are intended to include the plural forms as well, unless the context clearly indicates otherwise. Also, as used herein, "and/or" refers to and encompasses any and all possible combinations of one or more of the associated listed items.

Unless otherwise defined, all technical and scientific terms used herein have the same meaning as commonly understood by one of ordinary skill in the art to which this invention belongs. All publications, U.S. patent applications, U.S. patents and other references cited herein are incorporated by reference in their entireties with respect to the text referenced by the citation.

The present invention utilises ultrasonic energy to physically disrupt the collagenous architecture of natural biological matrices, ideally in a controlled manner so that the tissue can be rapidly and controllably recellularised in continuous form.

According to a first aspect of the invention there is provided a method of preparing tissue matrix for recellularisation comprising subjecting the tissue matrix to ultrasonic (US) energy.

Reference herein to recellularisation includes cellular infiltration and ingrowth of structures such as nerves, blood vessels and the tubular epithelioid vessels such as are found in the liver, kidneys, lung and pancreas into more complex 'organ' constructs.

Reference herein to tissue matrix includes a synthetic or natural (biological in origin) matrix that is either acellular or cellularised. The natural matrix may be autogeneic, allogeneic or xenogeneic.

Preferably, the US power applied to the surface of the tissue matrix is in the range of 1 to 1,000 Watts and more preferably is in the range 10 to 600 Watts, a typical value is about 300 Watts.

Preferably, the intensity of US energy on the surface of the tissue matrix is in the region of 0.05 to 50 Watts/mm$^2$ and more preferably still is in the range 0.5 to 50 Watts/mm$^2$ a typical value is about 3.0 Watts/mm$^2$.

Preferably, the US energy is applied to the surface of the tissue matrix from 1 second up to 1 hour, and more preferably is applied for about 1-10 minutes.

The US energy may be applied either as pulsed or continuous energy.

In the embodiment that the US energy is applied in pulse form, preferably the pulse is applied in the range 0.5 on 1 off to 10 on 1 off, and more preferably is applied as 3 on 1 off. The values are ratios of time on to time off typically seconds of time.

It will be appreciated that the power, intensity, pulse rate, area of tissue to be treated and duration of treatment is dependent on the tissue to be treated and the depth of recellularisation required.

Preferably, when US energy is applied to the surface of the tissue matrix it is bathed in an appropriate physiological medium such as aqueous saline.

Ultrasonication, i.e the application of high-frequency sound wave energy, has wide potential for the treatment of a range of natural soft tissues of autogeneic, allogeneic or xenogeneic origin, which might be used as temporary bioactive or resorbable matrices, or, as tissue engineered soft tissue implants.

Preferably, the method further includes the step of allowing or causing recellularisation of the tissue matrix either in vitro or, post-implantation, in vivo.

Accordingly, the method of the present invention can be performed on a tissue matrix prior to, during or even after implantation has occurred. Thus the method has potential use in static and bioreactive systems and in dynamic cultures.

An advantage of the method of the present invention is that ultrasonication does not render the tissue 'cell-type specific' in the way that some of the prior art methods may do and thus it can be utilised to enhance the cellular infiltration of a large number of cell types including: mesenchymal or stromal cells such as fibroblasts, smooth muscle cells, tenocytes, ligament cells, skeletal or cardiac myocytes, reticulo-endothelial cells and chondrocytes; neuroectodermal cells such as neurons, glial cells or astrocytes, endocrine cells (such as melanocytes, or adrenal, pituitary, or islet cells); and stem cells.

Preferably, the method further includes one or more additional treatments of the tissue matrix, in particular to facilitate recellularisation or successful implantation, for example, the step of applying an agent to the tissue matrix so as to enhance recellularisation.

Advantageously, the application of US is followed by the subsequent addition of potentially beneficial biological molecules, for example and without limitation growth factors and adhesion molecules, to the tissue matrix.

According to a further aspect of the invention there is provided use of ultrasonic energy for the manufacture of a tissue matrix for implantation, and optionally further including any one or more of the features hereinbefore described.

According to a further aspect of the invention there is provided use of ultrasonic energy for the manufacture of a tissue matrix for wound healing, and optionally further including any one or more of the features hereinbefore described.

According to a further aspect of the invention there is provided a method of preparing tissue matrix for wound healing comprising subjecting the tissue matrix to ultrasonic (US) energy, and optionally further including any one or more of the features hereinbefore described.

It is envisaged that the soft tissue implants engineered/manufactured using the method of the present invention have potential applications in the surgical replacement of: skin, bladder, intestine, colon, pericardium, blood vessels, heart valves, myocardium, muscle, cartilage, bone, meniscus, ligaments, tendons, cornea, urinary tract, urothelium, vagina, neural tissue and nerve. In addition, they may be used as 'patches' for internal wound closure or as biologically active 'bandages', which promote wound healing. In addition they may find use in the development of bioartificial devices for example as bioartificial organs the treatment of conditions arising from the impaired function of organs such as the pancreas, liver and kidney.

According to a further aspect of the invention there is provided a method of disrupting the collagenous network of a natural, soft tissue matrix by applying ultrasonic (US) energy so as to enhance cellular infiltration of the matrix.

Preferably the method includes any one or more of the features hereinbefore described.

Our results indicate that sonication provides a rapid, controlled and simple technique for disrupting the collagenous network of natural, soft tissue matrices with a view to enhancing cellular infiltration, either in vitro or in vivo. Because this technique is believed to modify tissues from the surface inwards, it enables both the biological and the physical properties of the treated matrix to be controlled. It will be appreciated that treatment conditions may be adjusted so that tissue can be modified to various depths. In this way, it may be possible to direct the migration of cells and hence predetermine their distribution to achieve uniformly dispersed, localised, or stratified cell patterning within the matrix whilst retaining adequate biomechanical function.

According to a yet further aspect of the invention there is provided an apparatus for preparing a tissue matrix for recellularisation comprising at least one means for delivering US energy to the tissue matrix, operatively linked to a US energy generator and a vessel for housing a tissue matrix in a physiological medium.

According to a further aspect of the invention there is provided an apparatus for preparing a tissue matrix for recellularisation comprising a vessel for housing a tissue matrix in a physiological medium and a US energy generator coupled to a delivery device which contacts or is in close proximity to the matrix and delivers US energy thereto.

Typically, the means for delivering US energy or delivery device is in the form of a probe. The probe is ideally a high intensity probe fitted with means for controlling the intensity of US energy delivered to the tissue matrix.

Preferably, the probe has a tip for contacting the tissue matrix and preferably the tip area, i.e. the area capable of delivering the US energy, is in the region of 10 to 1000 mm$^2$ and more preferably is about 100 mm$^2$.

Preferably, the apparatus further includes a cooling bath, typically an ice bath or a circulating water jacket of suitable dimensions for placing about/around the vessel containing the tissue matrix and physiological medium so as to cool the tissue matrix in the medium.

According to a yet further aspect of the invention there is provided a tissue matrix produced by the method of the present invention.

Preferably, the tissue matrix has a cell penetration depth after recellularisation of between 5 to 100% of the total tissue thickness.

Preferably, the tissue matrix may be used for the surgical replacement of, for example and without limitation, skin, bladder, intestine, colon, pericardium, blood vessels, heart valves, myocardium, muscle, cartilage, meniscus, ligaments, tendons, cornea, urinary tract, urothelium, vagina and nerve. In addition, they may be used as 'patches' for internal wound closure or as biologically active 'bandages', which promote wound healing and for the preparation of biomedical devices or bioartificial organs.

The invention will now be described by way of example only with reference to the following Figures wherein.

Figure 10A:
Figure 10B:
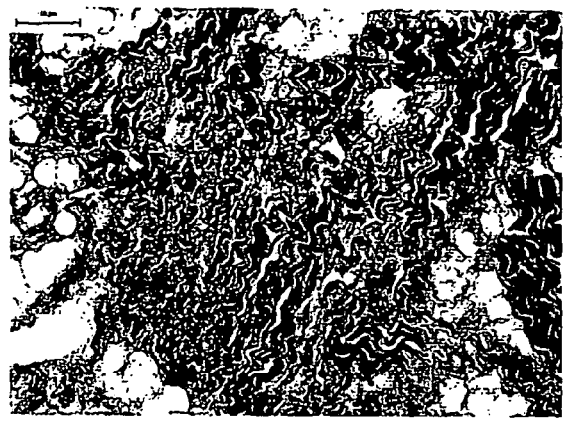
Figure 10C:
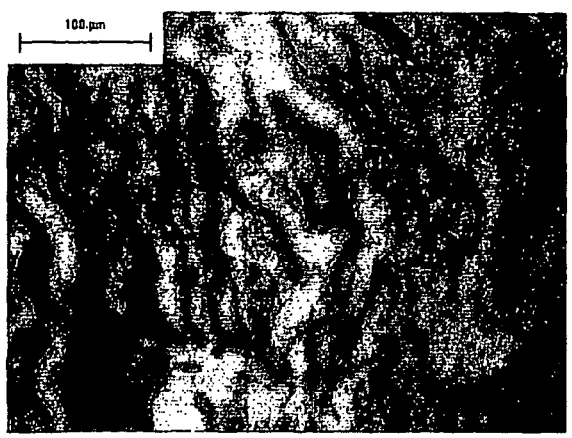
Figure 10D:
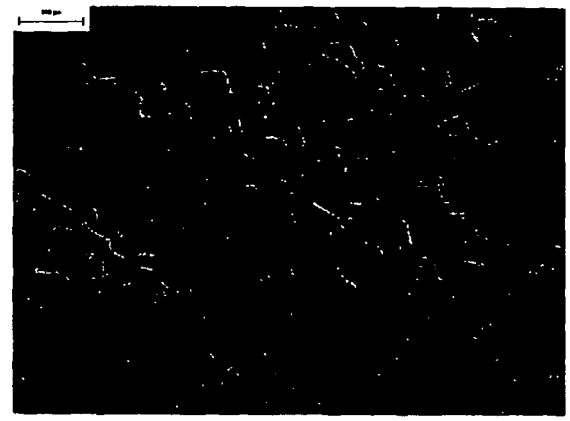

FIGS. 10A and B show cells within the matrix of sonicated porcine patella tendon following two and three weeks of culture respectively, FIG. 10C is a higher magnification of FIG. 10B and FIG. 10D is the untreated control.

Figure 11:
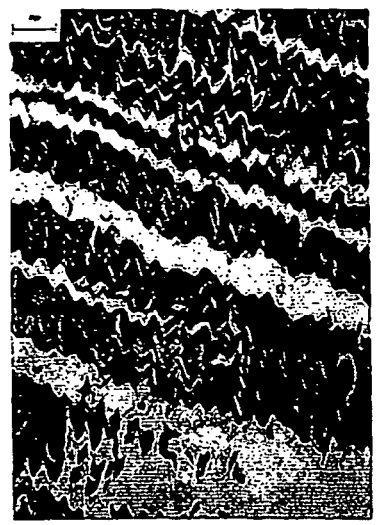
Figure 11:
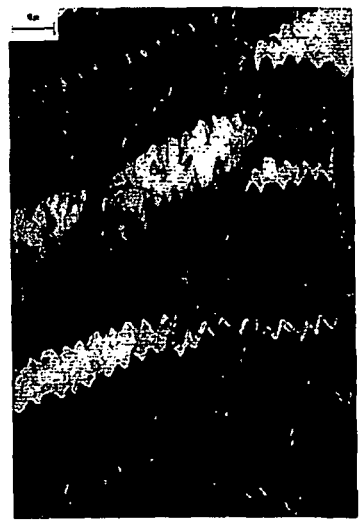
Figure 11:
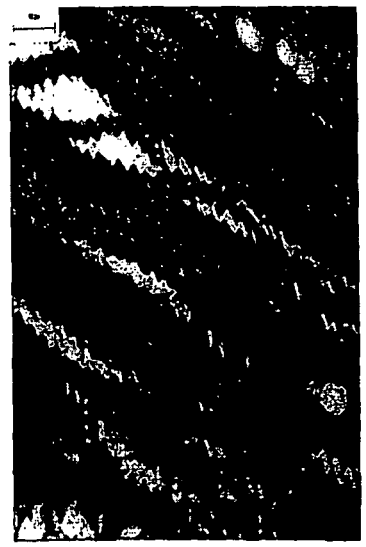

FIGS. 11A, 11B and 11C shows porcine patella tendons sonicated at 360 W at a 3 second pulse, 2 second pulse and 1 second pulse respectively.

Figure 12A:
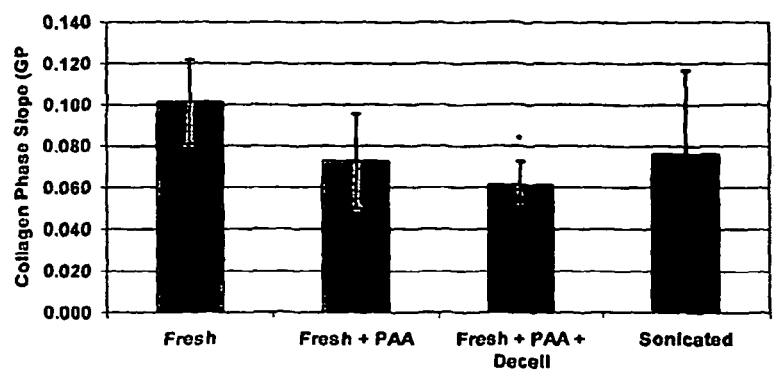
Figure 12B:
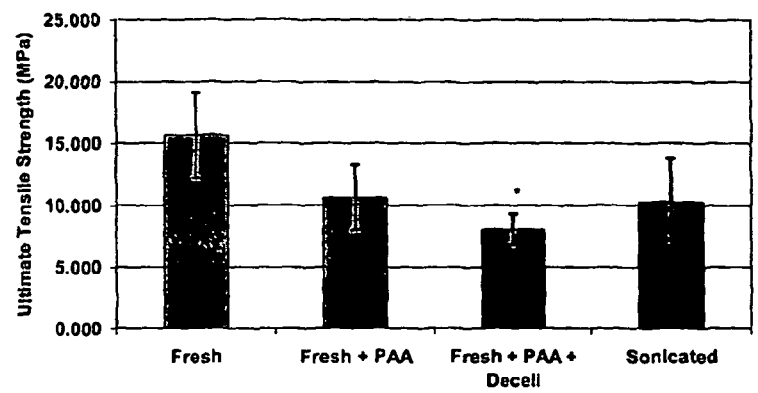
Figure 12C:
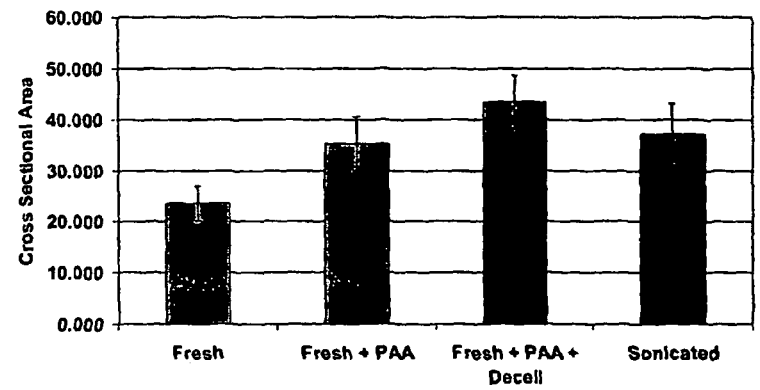
Figure 12:
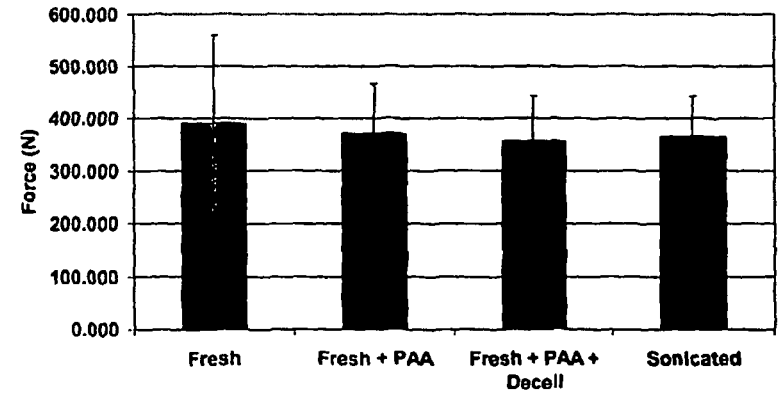

FIG. 12 shows bar charts of mechanical testing of fresh, decellarised and sonicated porcine patella tendons as collagen phase slope (FIG. 12A), ulimate tensile strength (FIG. 12B), cross sectional area (12C) and force (12D).

Figure 13:
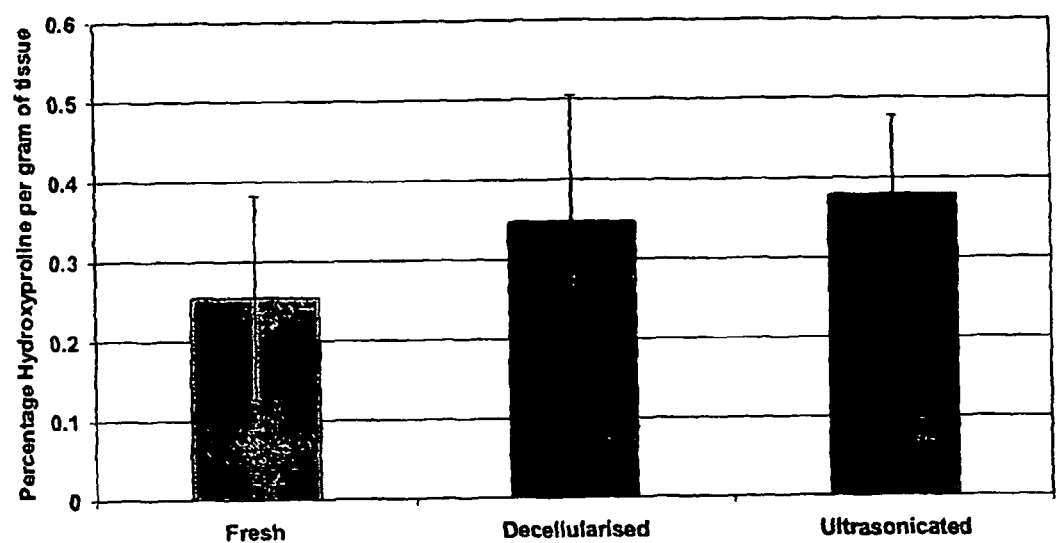

FIG. 13 shows a bar chart of alpha chymotrypsin assay of fresh, decellarised and sonicated porcine patella tendons.

DETAILED DESCRIPTION OF THE INVENTION

Figure 1:
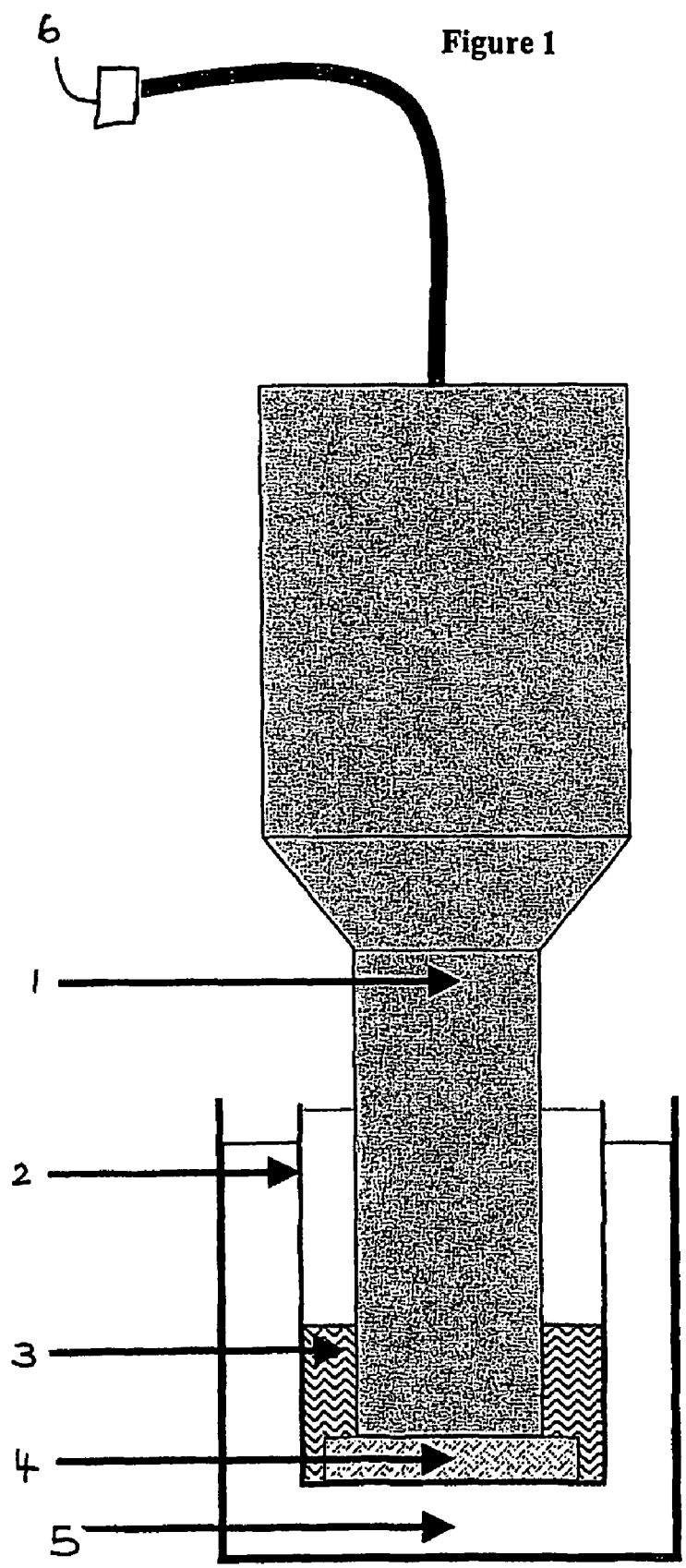
FIG. 1 represents a sonication apparatus.

The sonicator apparatus, as illustrated in FIG. 1, comprises a probe (1) connected to a sonicator control box (6). In use, the probe is made to rest on, or in close proximity to, a tissue matrix (4). The tissue matrix is placed in a bath or tissue holding vessel (2) containing a physiological medium (3), for example aqueous saline. Bath or tissue holding vessel (2) is surrounded by a cooling vessel (5) such as an ice bath or circulating water jacket.

Materials and Methods

Porcine Dermis

Permacol® matrix (acellular, isocyanate cross-linked, type I collagen scaffold derived from porcine dermis; Tissue Science Laboratories Ltd., Aldershot, UK) was cut into pieces sections approximately 1 cm$^2$. The matrix was then transferred to a Universal container containing 10 ml RPMI 1640 culture medium supplemented with 20 mM HEPES buffer, penicillin and streptomycin Tissue was then sonicated using a High Intensity Ultrasonic Processor (Model Number VC601; 600 W; Sonics and Materials, USA) fitted with a standard 13 mm (high intensity) probe. The sonicator was inserted into the culture medium and set at between 50 and 60 amplitude so that it delivered 300 W. Tissue sections were pulsed for 3 seconds on and 1 second off for a total time of 5 minutes (total duration of sonication=3.75 minutes).

Porcine Patella Tendon

Decellularised porcine patella tendon was sutured to a stainless steel grid and immersed in 500 ml of ice cold phosphate buffered saline in a glass beaker. The probe was lowered into the beaker to a depth of at least 2.5 inches. The tissue was sonicated using a high intensity Ultrasonic Processor (Model Number VC601; 600 W) fitted with a standard 13 mm (high intensity) probe. The sonicator was inserted into the medium and set at between 5% and 50% amplitude so that it delivered between 90 and 456 Watts. The Scaffold was pulsed for between 1 to 3 seconds on and 1 second off for a total time of 1 minute.

Primary Human Mononuclear Cells

Primary human mononuclear cells (PBMNC) were isolated from the heparinised peripheral blood of a healthy volunteer by density centrifugation over Lymphoprep® (Nycomed, Birmingham, UK). The proportion of mononuclear phagocytes (MP) was then determined using a latex bead ingestion assay. Sections of Permacol® matrix were then washed in phosphate buffered saline and cells were seeded at $10^5$ MP.cm$^{-2}$ in 50 μl RPMI 1640 culture medium supplemented with 10% (v/v) foetal calf serum, 20 mM L-glutamine, penicillin and streptomycin. Permacol® matrix, which had been subjected to sonication, was compared with untreated tissue. Cells were allowed to attach to the matrices for 1 hour at room temperature prior to washing away any non-adherent cells (e.g., lymphocytes) and flooding the wells with 2 ml supplemented RPMI 1640 culture medium. Cell seeded matrices were then incubated at 37° C. for a further i) 20 and ii) 96 hours after which time they were embedded in Cryo-M-Bed (Bright Instrument Co. Ltd., Cambridge, UK) and frozen quickly over dry ice. The embedded frozen tissues were then transferred to liquid nitrogen for storage. Cryosections were cut from the embedded frozen tissue (8 μm sections), stained with H and E using the standard protocol and examined by light microscopy to determine the tissue disruption and cell migration into tissue.

Primary Human Fibroblasts

Primary human fibroblasts were obtained from the National Blood Service—Tissue Services. Pieces of sonicated tendon scaffold (1 cm$^3$) were seeded at $1\times10^5$ cells.cm$^2$ in 1 ml of DMEM supplemented with 10% (v/v) foetal calf serum, 20 mM L, glutamine, penicillin and streptomycin. Untreated tendon scaffold was included as a control. Cells were allowed to adhere to the scaffold for 30 minutes at 37° C. prior to flooding the wells with 2 ml of supplemented DMEM. Cell seeded scaffolds were then incubated at 37° C. for up to 3 weeks with a treated and untreated cell seeded scaffold being removed every seven days after which the scaffolds were placed in 10% NBF and processed for routine histology. The embedded scaffolds were sectioned at 12 μm, stained with haematoxylin and eosin and examined by light microscopy to determine the tissue disruption and cell migration into the tissue.

EXAMPLE 1

Effect of Sonication on the Recellularisation and Matrix Disruption of Permacol®

Figure 2A:
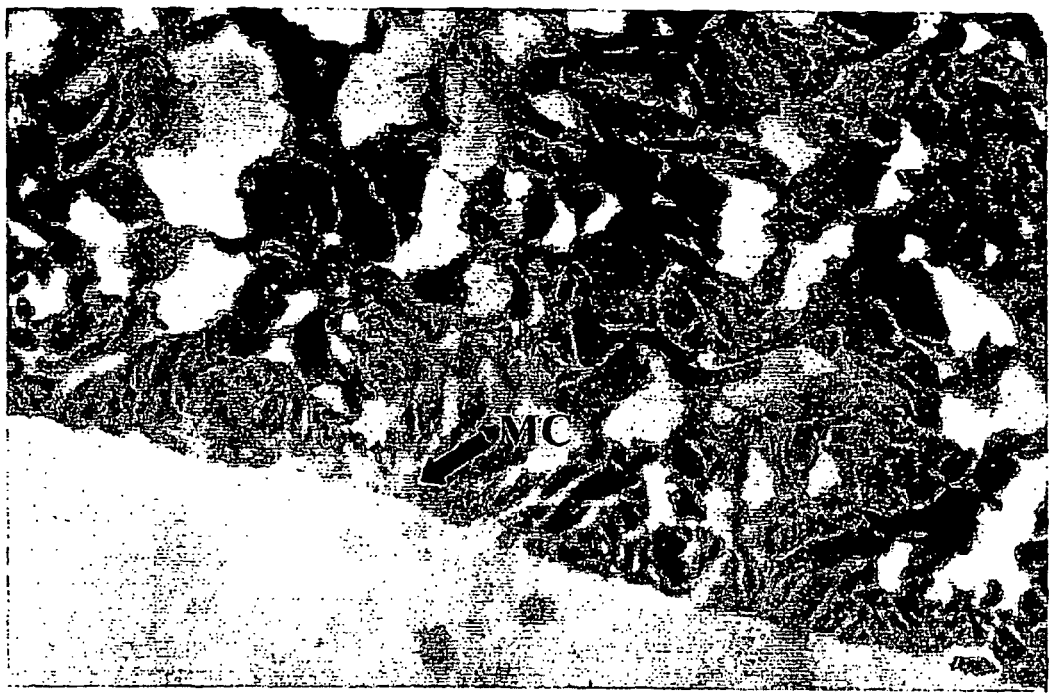
FIGS. 2A and 2B illustrate untreated Permacol® matrix plus human mononuclear phagocytes after 20 hours in culture at ×10 magnification.
Figure 2B:
Figure 3A:
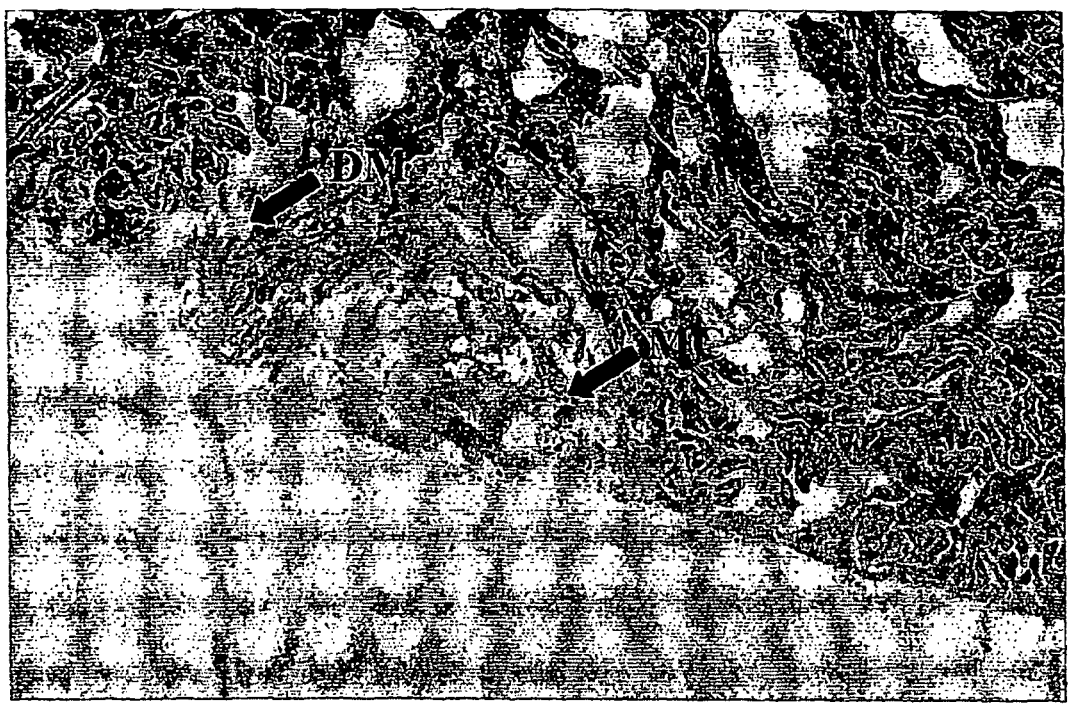
FIGS. 3A and 3B illustrate sonicated Permacol® matrix plus human mononuclear phagocytes after 20 hours in culture at ×10 magnification.
Figure 3:
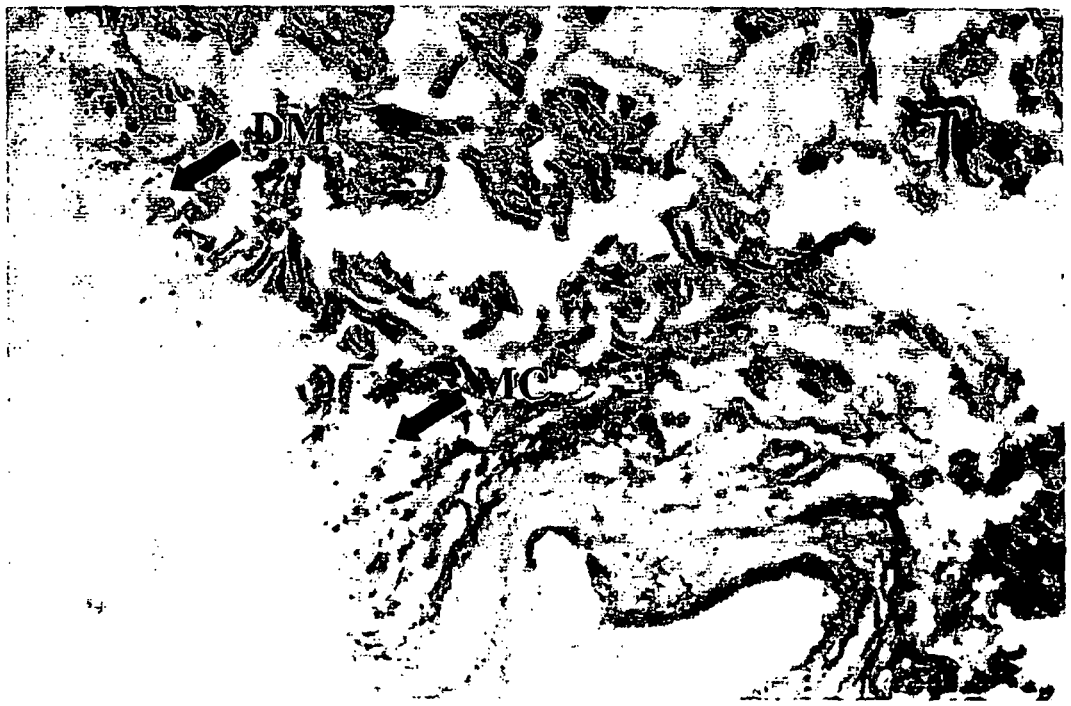
Figure 4A:
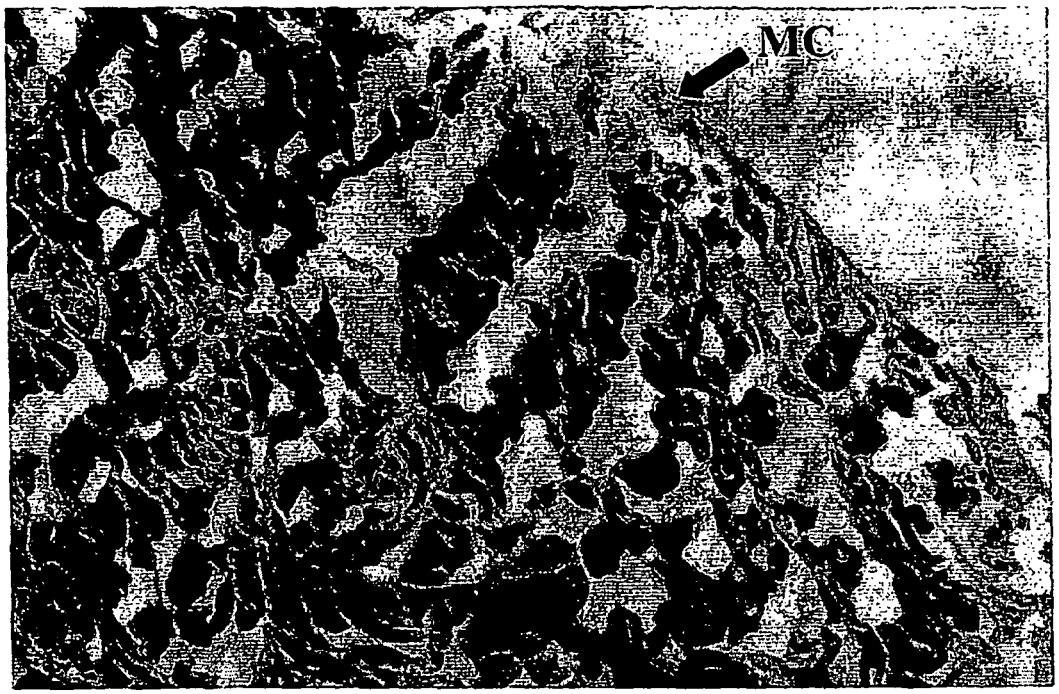
FIGS. 4A and 4C illustrate untreated Permacol® matrix plus human mononuclear phagocytes after 96 hours in culture at ×10 magnification.
Figure 4B:
FIGS. 4B and 4D illustrate untreated Permacol® matrix plus human mononuclear phagocytes after 96 hours in culture at ×20 magnification.
Figure 4C:
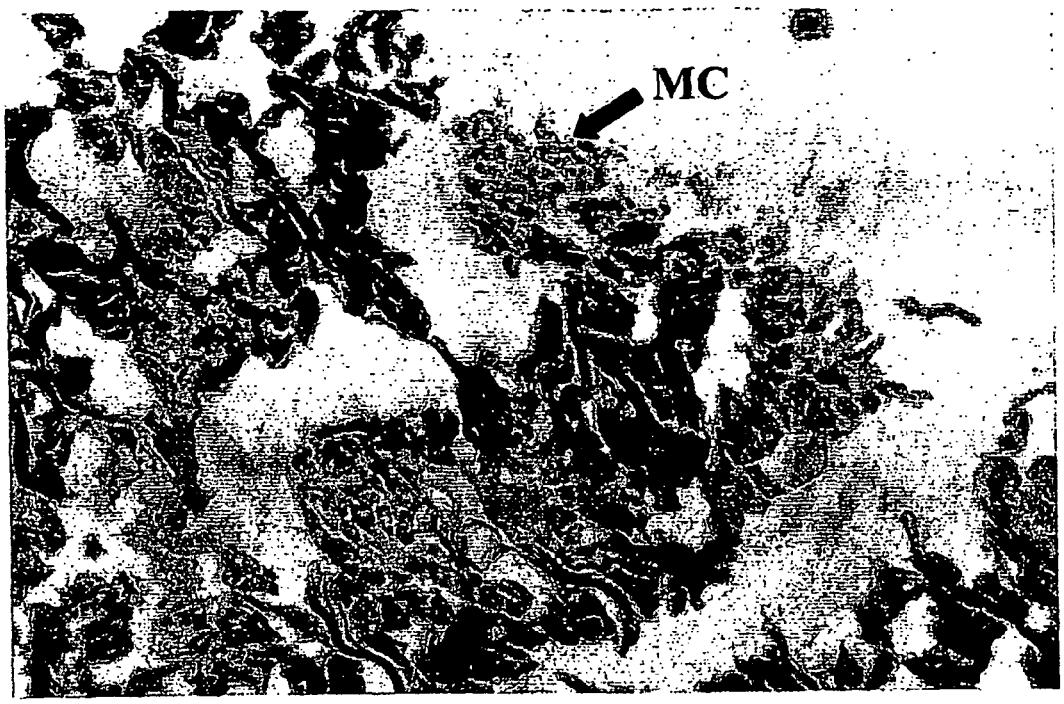
Figure 4D:
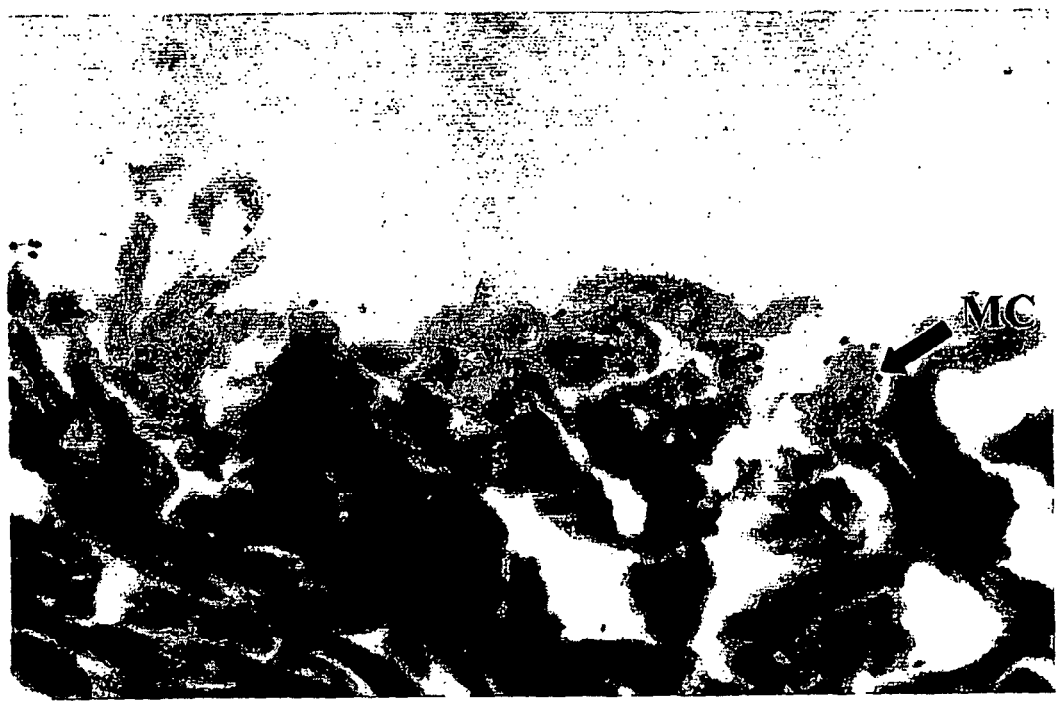
Figure 5A:
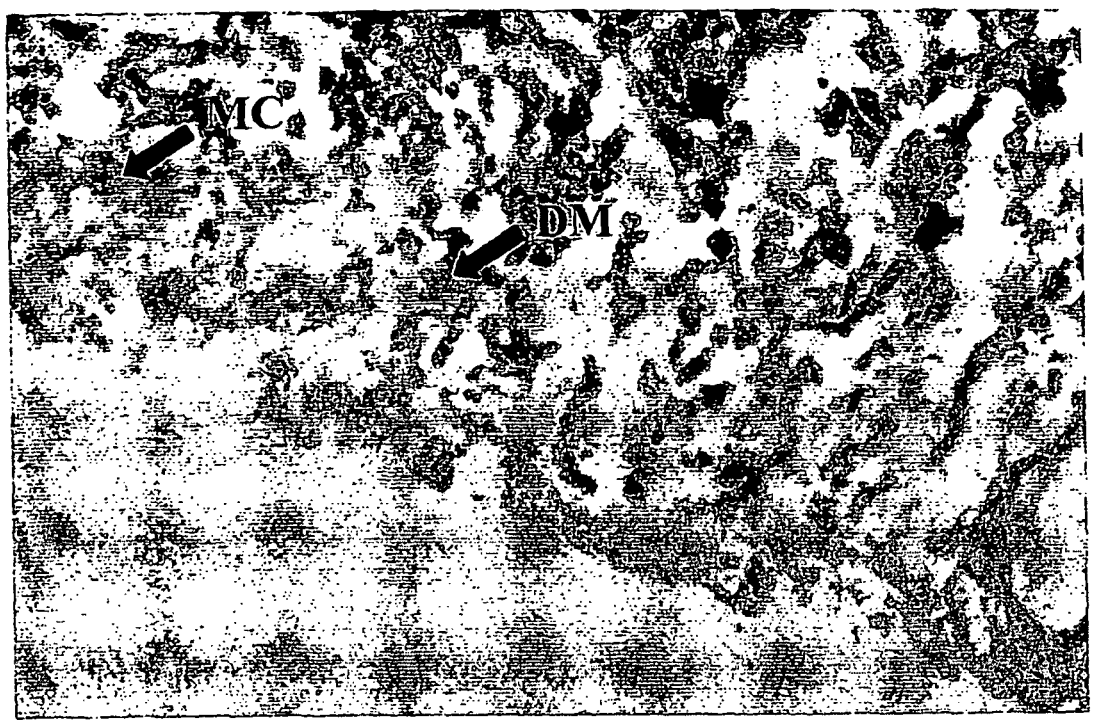
FIGS. 5A and 5C illustrate sonicated Permacol® matrix plus human mononuclear phagocytes after 96 hours in culture at ×10 magnification.
Figure 5B:
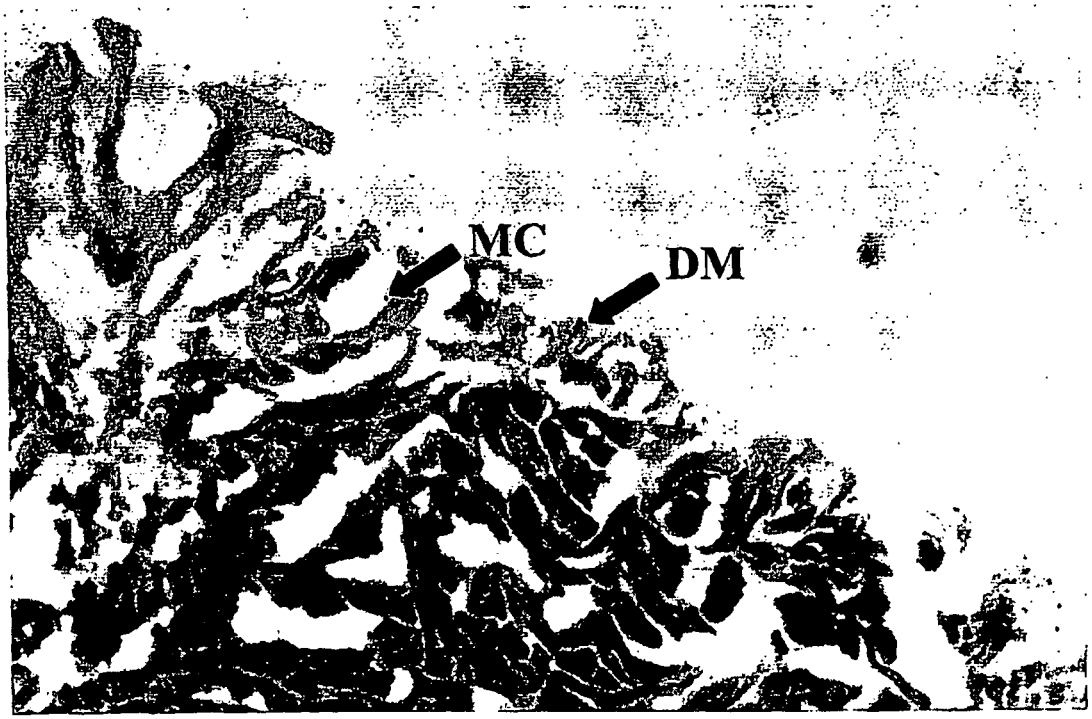
FIGS. 5B and 5D illustrate sonicated Permacol® matrix plus human mononuclear phagocytes after 96 hours in culture at ×20 magnification.
Figure 5C:
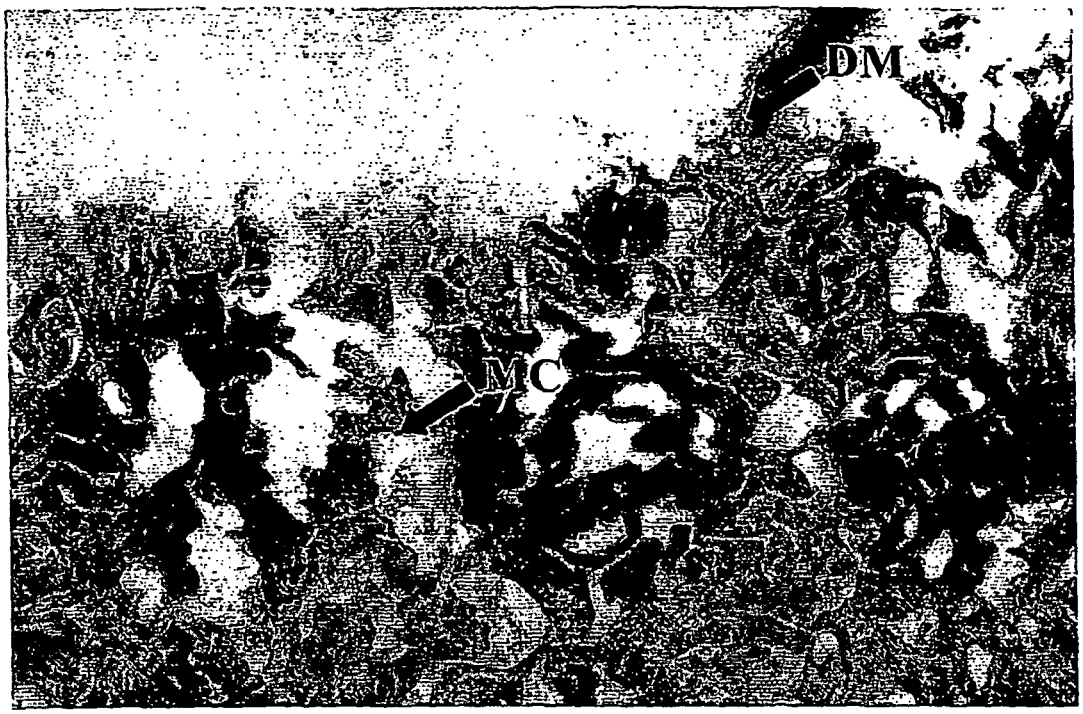
Figure 5D:
Figure 6A:
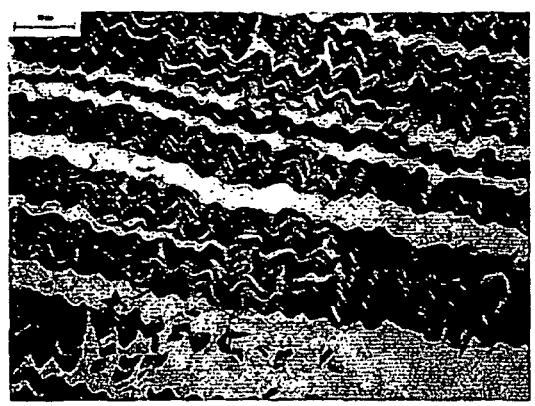
FIGS. 6A, 6B, 6C and 6D shows porcine patella tendon scaffold treated with 380 W, 409 W, 437 W and 456 W ultra-sonication respectively.
Figure 6B:
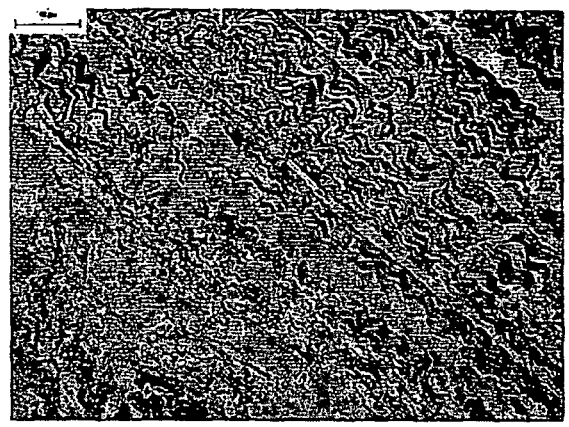
Figure 6C:
Figure 6D:
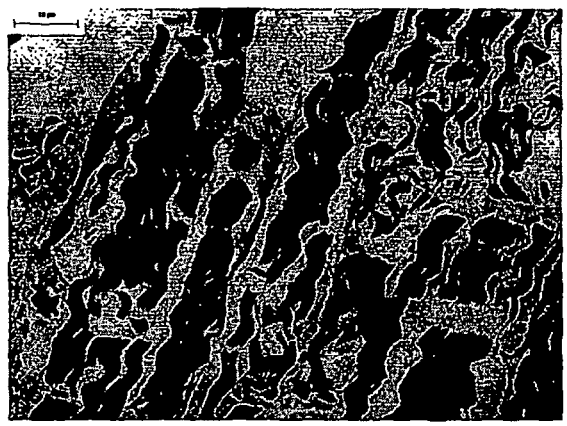

After sonication, Permacol® tissue appeared more diffuse than the untreated 'control' tissue when evaluated by gross visual inspection. Histological evaluation determined that low but similar numbers of cells were attached to the surface of both 'control' (FIGS. 2A and 2B) and sonicated Permacol® (FIGS. 3A and 3B) matrices after 20 hours in culture and there was an indication that this number increased slightly with time. Furthermore, by 96 hours, cells appeared to have begun to penetrate into the matrices. However, the matrix architecture of the 'control' Permacol® varied immensely within each histological section and correspondingly, cell 'penetration' was not uniform across the surface of the tissue (FIGS. 4A, 4B, 4C and 4D). Areas of major cellular 'penetration' were largely confined to the small naturally occurring diffuse regions and super-structures such as hair follicles and glands, in the untreated Permacol®. However, cells tended to line these features rather than gain entry to the inner matrix via them. In comparison, the follicles and surfaces of sonicated Permacol® (FIGS. 5A, 5B, 5C and 5D) appeared to be more diffuse than control tissue. This tissue disruption and the associated cell penetration appeared to reach a depth of around $\frac{1}{10}^{th}$ of the total tissue thickness (~150 μm).

EXAMPLE 2

Effect of Sonication on the Matrix Disruption and Recellularisation of Decellularised Porcine Tendon Scaffold.

Figure 7A:
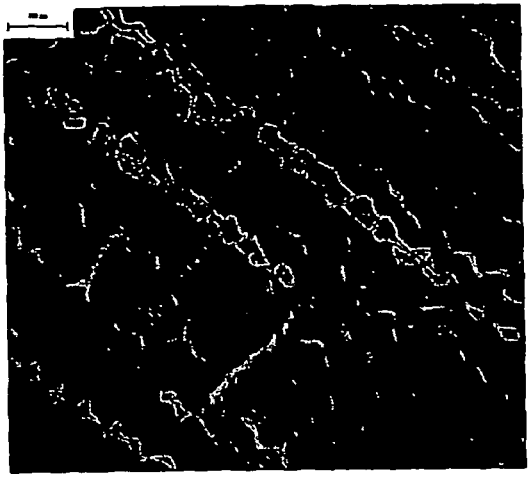
FIGS. 7A and 7B shows porcine patella tendon scaffold treated with 90 W and 360 W ultra-sonication respectively.
Figure 7B:
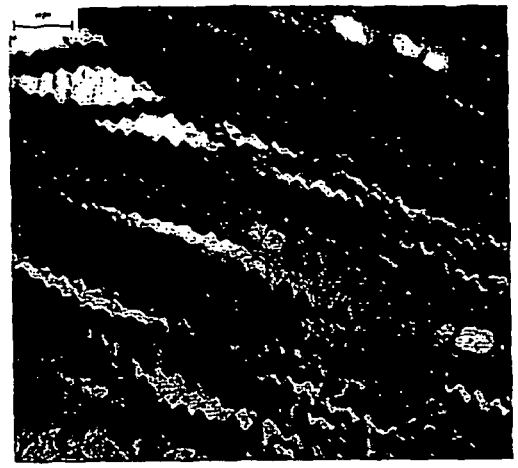
Figure 8:
FIG. 8 shows a control untreated porcine patella tendon scaffold.
Figure 9:
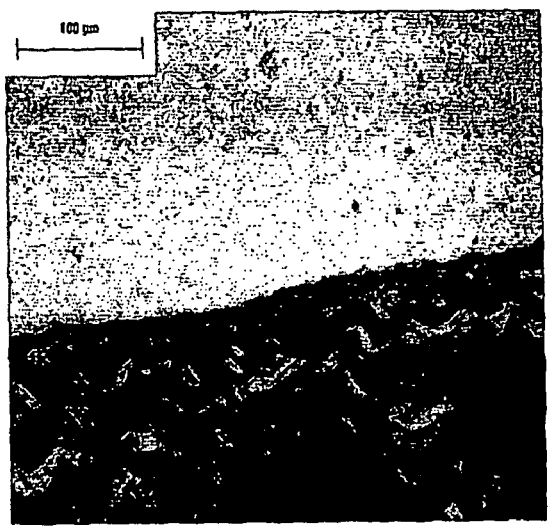
FIG. 9 shows a tenocyte monolayer growing on the surface of a sonicated porcine patella tendon following one week of culture.

Following sonication the decellularised scaffold the scaffold ultra structure appeared unchanged at low power however when sonicated at high power the scaffold looked like wet cotton wool. Histological evaluation showed that high power ultrasonictaion left the matrix unrecognisable (FIGS. 6A, 6B, 6C and 6D) as tendon tissue with large holes and breaks in the collagen structure with, in some cases, disruption of tendon fascicles. However low power sonication left the matrix intact (FIG. 7A and 7B) as compared to the control in FIG. 8. At 90 W sonication no obvious changes in the matrix were observed and at 360 W sonication whilst opening up the spaces between collagen bundles that the cells would occupy there was no evidence of damage to the collagen itself. FIG. 8 shows an untreated scaffold with small openings between collagen fibres where the cells were removed during decellularisation. Histological examination also determined that cells (tenocytes) were able to attach to the surface of the sonicated scaffold as a monolayer after 24 hours of culture (FIG. 9). This was also observed for the untreated control group. Following further culture time two weeks (FIG. 10A) and three week (FIGS. 10B and C) the cells were observed to have penetrated deeper into the sonicated scaffold whilst in the non treated group (FIG. 10D) the cells were not able to penetrate further than the surface of the tendon. The penetration of cells into the sonicated tendon reached the central portion of the scaffold after three weeks of culture.

With reference to FIGS. 11A, 11B and 11C there is shown pictures of tendons sonicated at 360 W but with different pulse times 3, 2, and 1 second respectively that is to say 3 seconds on 1 off and so on. The results demonstrate that at 360 W gaps are formed between collagen bundles but no damage to collagen occurs. It appears from these pictures that a pulse time of 1 second gives a more even distribution of gaps and that these are of equal size.

Evaluation of the biochemistry of the scaffold showed no decrease in either the hydroxyproline (measure of collagen) or glycosaminoglycan content of the scaffold.

Biomechanical testing (FIG. 12) showed that whilst the collagen phase slope and therefore ultimate tensile strength of the decellularised scaffold were significantly reduced when compared to fresh tissue this was not the case for the sonicated scaffold which showed increases in these properties compared to the decellularised scaffold. Further investigation found this to be due to the changing cross sectional area of the scaffold following various treatments and therefore the ultimate force (N) was used as comparison of the mechanical properties of the scaffolds. With reference to FIG. 12 the bar charts show width of the tendons and their corresponding force measurements. There appears to be no difference in the force needed to break the tendon after any treatments.

The mechanical tests were carried out on fresh patella tendon, fresh tendon sterilised with 0.1% peractic acid (PAA), decellularised tendon (0.1% SDS) that was sterilised with PAA and finally a decellularised, sterilised tendon that was then sonicated (360 W) prior to mechanical testing.

The ultimate tensile strength is the parameter most commonly used to describe the mechanical characteristics of this tissue and in this study the decellularised scaffold has a significantly lower UTS than fresh tissue. However when the scaffold was sonicated this value returned to a non-significant level. This is due to the changing cross sectional area of the scaffold following each treatment. In order to negate this it was decided to use ultimate force as a measure of mechanical properties as this takes into account the changes in cross sectional area.

Biochemical data on the sonicated scaffold was obtained using alpha-chyma trypsin assay. This enzyme only cleaves damaged collagen so if sonication has caused any damage to the collagen, levels of hydroxyproline will be higher than in non-treated scaffolds contains the alpha chymotrypsin assay data This measures denatured collagen. The results show that collagen is not damaged by ultrasonication when compared to fresh tissue (FIG. 13).

The present invention therefore provides a method of utilising ultrasonic energy to mechanically disrupt the collagenous structure of a tissue matrix in a controlled manner so that the tissue matrix can be rapidly recellularised in a continuous manner. Accordingly, it is possible to direct the migration of cells and hence predetermine their distribution to achieve uniformly dispersed, localised, or stratified cell patterning within the matrix whilst retaining adequate biomechanical function.

The invention claimed is:

1. A method of preparing an acellular, biomechanically intact, collagenous tissue matrix having a scaffold ultrastructure for recellularization, the method comprising subjecting an intact, acellular collagenous tissue matrix having a scaffold ultrastructure to ultrasonic (US) energy ex vivo, wherein the ultrasonic energy is applied in an amount which is sufficient to form gaps between collagen bundles while leaving the collagenous matrix ultrastructure intact, wherein subjecting said acellular collagenous tissue matrix having a scaffold ultrastructure to the ultrasound energy improves the recellularization and/or cellular infiltration of the tissue matrix.

2. A method according to claim 1 wherein the US power on the surface of the acellular tissue matrix is in the range of 1 to 1,000 Watts.

3. A method according to claim 2 wherein the US power range is in the range of 10 to 600 Watts.

4. A method according to claim 3 wherein the US power is about 300 Watts.

5. A method according to claim 1 wherein intensity of US energy on the surface of the acellular tissue matrix is in the region of 0.01 to 50 Watts/mm$^2$.

6. A method according to claim 5 wherein the US energy is in the region of 0.01 to 50 Watts/mm$^2$.

7. A method according to claim 6 wherein the US energy is about 3.0 Watts/mm$^2$.

8. A method according to claim 1 wherein the US energy is supplied to the surface of the acellular tissue matrix for a period of time in a range from 1 second to 1 hour.

9. A method according to claim 8 wherein the US energy is supplied for a period of time in a range from 1 to 10 minutes.

10. A method according to claim 1 wherein the US energy is applied as pulsed or continuous energy.

11. A method according to claim 10 wherein pulsed US energy is applied in the range 0.5 on 1 off to 10 on 1 off.

12. A method according to claim 11 wherein the energy is applied as 3 on 1 off.

13. A method according to claim 1 wherein the acellular tissue matrix is bathed in a physiological medium.

14. A method according to claim 13 wherein the medium is physiological saline.

15. A method according to claim 1 further including the step of recellularizing the acellular tissue matrix either in vitro or, post-implantation, in vivo.

16. A method according to claim 15 wherein the acellular tissue matrix is recellularized by at least one cell type selected from the group consisting of: mesenchymal or stromal cells, fibroblasts, smooth muscle cells, tenocytes, ligament cells, skeletal or cardiac myocytes, reticulo-endothelial cells, chondrocytes, neuroectodermal cells, neurons, glial cells, astrocytes, endocrine cells, melanocytes, adrenal, pituitary, or islet cells and stem cells.

17. A method according to claim 1 further comprising one or more additional treatments of the acellular tissue matrix to facilitate recellularization or successful implantation.

18. A method according to claim 17 wherein the additional treatment is a growth factor and/or an adhesion molecule.

19. A method according to claim 1 wherein the acellular tissue matrix has a cell penetration depth after recellularization of between 5 to 100% of the total acellular tissue matrix thickness.

20. A method according to claim 1, wherein the acellular tissue matrix is configured for implantation.

21. A method according to claim 1 wherein the gaps between collagen bundles are formed without damage to the collagen.

22. A method according to claim 1 wherein after subjecting the acellular, intact, tissue matrix to ultrasonic (US) energy, the biomechanical function of the acellular tissue matrix scaffold ultrastructure is retained.

23. A method according to claim 1 wherein collagen of the acellular tissue matrix is not damaged by ultrasonication.

24. A method according to claim 1 wherein the acellular tissue matrix is configured to direct a migration of cells and to predetermine a distribution of the cells to achieve uniformly dispersed, localized or stratified cell patterning within the acellular tissue matrix.

25. A method according to claim 1 further comprising applying the US energy using an ultrasound probe configured to contact or be held in close proximity to the acellular tissue matrix.

26. A method according to claim 20 further comprising applying the US energy using an ultrasound probe configured to contact or be held in close proximity to the acellular tissue matrix.

* * * * *

UNITED STATES PATENT AND TRADEMARK OFFICE
CERTIFICATE OF CORRECTION

| | | |
|---|---|---|
| PATENT NO. | : 7,754,232 B2 | Page 1 of 1 |
| APPLICATION NO. | : 10/557779 | |
| DATED | : July 13, 2010 | |
| INVENTOR(S) | : Fisher et al. | |

It is certified that error appears in the above-identified patent and that said Letters Patent is hereby corrected as shown below:

In the Patent:
Column 6, Line 13: Please correct "streptomycin" to read -- streptomycin. --

Column 8, Line 43: Please correct "data" to read -- data. --

In the Claims:
Column 8, Claim 1, Line 66-67: Please correct "rccellularization"
                                                                to read -- recellularization --

Signed and Sealed this
Twenty-second Day of January, 2013

David J. Kappos
*Director of the United States Patent and Trademark Office*